United States Patent
Harris et al.

(10) Patent No.: US 7,041,863 B2
(45) Date of Patent: May 9, 2006

(54) ZEOLITE Y ALKYLATION CATALYSTS

(75) Inventors: Thomas V. Harris, Benicia, CA (US); Curt B. Campbell, Hercules, CA (US); Paul J. Marcantonio, San Rafael, CA (US); Pierre Tequi, Breaute (FR); Jean-Louis Le Coent, Le Havre (FR)

(73) Assignees: Chevron Oronite Company LLC, San Ramon, CA (US); Chevron Oronite S.A., Argenteuil (FR)

( * ) Notice: Subject to any disclaimer, the term of this patent is extended or adjusted under 35 U.S.C. 154(b) by 0 days.

(21) Appl. No.: 11/186,156

(22) Filed: Jul. 20, 2005

(65) Prior Publication Data

US 2005/0250970 A1    Nov. 10, 2005

Related U.S. Application Data

(62) Division of application No. 10/800,047, filed on Mar. 12, 2004.

(51) Int. Cl.
*C07C 2/66* (2006.01)
*C10M 105/66* (2006.01)

(52) U.S. Cl. .......... 585/467; 560/30; 560/32; 560/33; 508/198

(58) Field of Classification Search .......... 585/467; 560/30, 32, 33; 508/198
See application file for complete search history.

(56) References Cited

U.S. PATENT DOCUMENTS 4,123,390 A * 10/1978 Sherman et al. ............ 426/561
5,118,896 A * 6/1992 Steigelmann et al. ....... 585/467

* cited by examiner

*Primary Examiner*—Elizabeth D. Wood
(74) *Attorney, Agent, or Firm*—Sarita R. Kelley

(57) ABSTRACT

The present invention is directed to a zeolite Y catalyst having a controlled macropore structure. The present invention is also directed to a zeolite Y catalyst composite and a process for preparing the catalyst composite. The catalyst composite exhibits reduced deactivation rates during the alkylation process, thereby increasing the life of the catalyst. The present invention is also directed to processes for the preparation of carbonated, overbased aromatic sulfonates, which processes comprise alkylation, carbonation of aromatic hydrocarbons with one or more olefins.

16 Claims, No Drawings

ZEOLITE Y ALKYLATION CATALYSTS

This application is a Divisional of application Ser. No. 10/800,047, filed Mar. 12, 2004.

FIELD OF THE INVENTION

The present invention is directed to a zeolite Y catalyst having a controlled macropore structure. The present invention is also directed to a catalyst composite comprising zeolite Y and a process for preparing the catalyst composite. The present invention is also directed to alkylation of aromatic hydrocarbons using the catalysts and the catalyst composites of this invention, and the sulfonation and carbonation of the alkylated aromatic hydrocarbons. The catalysts and the catalyst composites exhibit reduced deactivation rates during the alkylation process, thereby increasing the life of the catalyst.

BACKGROUND OF THE INVENTION

It is well known to catalyze the alkylation of aromatics with a variety of Lewis or Bronsted acid catalysts. Typical commercial catalysts include phosphoric acid/kieselguhr, aluminum halides, boron trifluoride, antimony chloride, stannic chloride, zinc chloride, onium poly(hydrogen fluoride), and hydrogen fluoride. Alkylation with lower molecular weight olefins, such as propylene, can be carried out in the liquid or vapor phase. For alkylations with higher olefins, such as $C_{16}$ olefins, the alkylations are done in the liquid phase, usually in the presence of hydrogen fluoride. Alkylation of benzene with higher olefins is especially difficult, and requires hydrogen fluoride treatment. However, hydrogen fluoride is not environmentally attractive.

The use of the above listed acids is extremely corrosive, thus requiring special handling and equipment. Also, the use of these acids might involve environmental problems. Another problem is that the use of these acids can give less than desirable control on the precise chemical composition of the product produced. Thus, it would be preferable to use a safer, simpler catalyst, preferably in solid state. This simpler process would result in less capital investment, which would result in a less expensive product.

Solid crystalline aluminosilicate zeolite catalysts have been known to be effective for the alkylation of aromatics with olefins. Zeolitic materials which are useful as catalysts are usually inorganic crystalline materials that possess uniform pores with diameters in the micropore range that is less than 20 angstroms. Zeolites occur naturally and may also be prepared synthetically. Synthetic zeolites include, for example, zeolites A, X, Y, L and omega. It is also possible to generate metaloaluminophosphates and metalosilicophosphates. Other materials, such as boron, gallium, iron or germanium, may also be used to replace the aluminum or silicon in the framework structure.

These zeolite catalyst materials are commercially available as fine crystalline powders for further modification to enhance their catalytic properties for particular applications. Processes for the further modification to enhance catalytic properties of the crystalline zeolite catalysts are well known in the art, such as forming the zeolite catalysts into shaped particles, exchanging the cations in the catalyst matrix, etc.

Forming the zeolite powders into shaped particles may be accomplished by forming a gel or paste of the catalyst powder with the addition of a suitable binder material such as a clay, an inorganic compound, or an organic compound and then extruding the gel or paste into the desired form. Zeolite powders may also be formed into particles without the use of a binder. Typical catalyst particles include extrudates whose cross sections are circular or embrace a plurality of arcuate lobes extending outwardly from the central portion of the catalyst particles.

One problem with catalyst particles used in fixed bed reactors is catalyst deactivation. In most hydrocarbon conversion processes, including alkylation, the primary catalyst deactivation is caused by coke formation. This catalyst deactivation is a serious problem in the use of zeolite catalysts for alkylation reactions. This deactivation problem is well known in the art and it is well understood that the deactivation mechanism can involve polymerization of the olefin into large molecular species that cannot diffuse out of the pores containing the active sites in the zeolitic material.

The use of zeolite catalysts for preparation of alkyl aromatics is typically conducted by the catalytic alkylation of aromatic hydrocarbons with normal alpha olefins or branched-chain olefins, and optionally a promotor. The alkylated aromatic hydrocarbons can be converted into corresponding sulfonic acids which can be further converted into alkylated aromatic sulfonates.

A number of patents have discussed processes for the preparation of zeolite catalysts and the further shaping and forming of the catalyst particles and extrudates with and without the use of binders. There are also a number of patents disclosing the use of zeolite catalysts for alkylation of aromatic hydrocarbons.

U.S. Pat. No. 3,094,383 discloses the preparation of synthetic zeolite materials which upon hydration yield a sorbent of controlled effective pore diameter and in which the sorbent and its zeolite precursor are provided directly in the form of an aggregate.

U.S. Pat. No. 3,130,007 discloses the method of preparing sodium zeolite Y with silica to alumina ratios ranging from greater than 3 to about 3.9.

U.S. Pat. No. 3,119,660 discloses a process for making massive bodies or shapes of crystalline zeolites. The patent also discloses methods for the identification of the catalyst materials using X-ray powder diffraction patterns in conjunction with chemical analyses.

U.S. Pat. No. 3,288,716 discloses that the high "heavy content" of the alkylated aromatic product can be controlled during the alkylation step and has advantages over distilling the alkylated aromatic product to obtain the desired molecular weight.

U.S. Pat. Nos. 3,641,177 and 3,929,672 disclose the technique to remove sodium or other alkali metal ions from zeolite catalysts. The '177 patent also discloses that such removal of the sodium or other alkali metal ions activates the zeolite catalysts for the alkylation of aromatic hydrocarbons with olefins by liquid phase reaction.

U.S. Pat. Nos. 3,764,533; 4,259,193 and 5,112,506 disclose the "heavy alkylate" content influences neutral sulfonates and overbased sulfonates. In U.S. Pat. No. 5,112,506, the effect of molecular weight distribution or "heavy alkylate" is shown to influence the performance of both Neutral and HOB sulfonates and the di-alkylate content is shown to influence the rust performance of the corresponding sulfonate in U.S. Pat. No. 3,764,533. In U.S. Pat. No. 4,259,193, a mono-alkylate sulfonate is preferred. U.S. Pat. Nos. 3,288,716; 3,764,533; 4,259,193 and 5,112,506 are hereby incorporated by reference for all purposes.

U.S. Pat. No. 3,777,006 discloses the use of nucleating centers for the crystallization of crystalline aluminosilicate zeolites having a size in excess of 200 microns and characterized by high strength and excellent adsorptive properties.

U.S. Pat. No. 4,185,040 discloses the preparation of highly stable and active catalysts for the alkylation of aromatic hydrocarbons with $C_2$–$C_4$ olefins. The catalysts are acidic crystalline aluminosilicate zeolites which exhibit much improved deactivation rates.

U.S. Pat. No. 4,395,372 discloses an alkylation process for alkylating benzene comprising contacting benzene and lower olefins with a rare earth exchanged X or Y zeolite catalyst in the presence of sulfur dioxide.

U.S. Pat. No. 4,570,027 discloses the use of a low crystallinity, partially collapsed zeolite catalyst for producing alkylaromatic hydrocarbons. The alkylation reaction also involves conditioning the catalyst bed with hydrogen prior to conducting the alkylation reaction.

U.S. Pat. Nos. 4,762,813; 4,767,734; 4,879,019 and 5,111,792 disclose the preparation of a hydrocarbon conversion catalyst using a low silica to alumina ratio zeolite Y bound into an extrudate and steamed to modify the catalyst.

U.S. Pat. No. 4,764,295 discloses a process for making non-foaming detergent-dispersant lubricating oil additives. The process further involves carbonation for making the products more basic.

U.S. Pat. No. 4,876,408 discloses an alkylation process using an ammonium-exchanged and steam stabilized zeolite Y catalyst having an increased selectivity for mono-alkylation the process involves the presence of at least one organic compound under conditions such that sufficient amount of carbonaceous material evenly deposits on the alkylation catalyst to substantially suppress its alkylation activity.

U.S. Pat. No. 4,916,096 discloses use of a zeolite Y catalyst for hydroprocessing. The zeolite Y catalyst comprises a modified crystalline aluminosilicate zeolite Y, a binder and at least one hydrogenation component of a Group VI or a Group VIII metal.

U.S. Pat. No. 5,026,941 discloses the use of a zeolite Y catalyst having a silica to alumina molar ratio of 15 to 110 for the alkylation of naphthalene or mono-isopropylnaphthalene.

U.S. Pat. No. 5,118,896 discloses an aromatic alkylation process comprising the steps of contacting an aromatic hydrocarbon feed with an alkylating agent under liquid phase alkylation conditions in the presence of a silica-containing large macropore, small particle size zeolite catalyst, the catalyst having a pore volume of about 0.25 to 0.50 cc/g in pores having a radius of 450 angstroms and a catalyst particle diameter of not more than 1/32 of an inch.

U.S. Pat. No. 5,191,135 discloses the process for making long-chain alkyl-substituted aromatic compounds from naphthalenes, the process comprising a zeolite alkylation catalyst in the presence of 0.5 to 3.0 weight percent water. The presence of water increases the selectivity for making mono-alkylated products.

U.S. Pat. Nos. 5,240,889 and 5,324,877 disclose processes for the preparation of a catalyst composition having alkylation and/or transalkylation activity and wherein the catalyst composition contains greater than 3.5 weight percent water based on the total weight of the catalyst composition and the aromatic alkylation process using said catalyst composition and olefins containing 2 carbon atoms to 25 carbon atoms.

U.S. Pat. No. 5,506,182 discloses the preparation of a catalyst composition comprising 10 to 90 percent of a modified zeolite Y catalyst formed from a modified zeolite Y and 10 to 90 percent binder using slurries of the modified zeolite Y and the binder to form the catalyst composition having a clear absorption peak in an IR spectrum of a wavelength of 3602 per centimeter. The patent also discloses the substitution of iron for the alumina in the zeolite Y structure.

U.S. Pat. No. 5,922,922 discloses a process for isomerizing a normal alpha olefin in the presence of an acidic catalyst having a one-dimensional pore system, and then using of the isomerized olefin to alkylate aromatic hydrocarbons in the presence of a second acidic catalyst, which can be zeolite Y having a silica to alumina ratio of at least 40 to 1.

U.S. Pat. No. 5,939,594 discloses the preparation of a superalkalinized alkylaryl sulfonate of alkaline earth metal. The alkyl group of the alkylaryl sulfonate contains between 14 to 40 carbon atoms and the aryl sulfonate radical of alkaline earth metal is fixed in a molar proportion comprised between 0 and 13% in positions 1 or 2 of the linear alkyl chain.

U.S. Pat. No. 6,031,144 discloses a process for reducing the residual olefin content of an alkylation reaction product by removing at least a portion of the non-alkylated single-ring aromatic hydrocarbon and then reacting the remaining alkylation reaction product in the presence of an acidic catalyst such as a molecular sieve or clay.

U.S. Pat. No. 6,337,310 discloses the preparation of alkylbenzene from preisomerized normal alpha olefins for making low overbased and high overbased sulfonates having a TBN in the range of 3 to 500. The process uses HF as catalyst or a solid acidic alkylation catalyst, such as a zeolite having an average pore size of at least 6 angstroms.

It is known that most solid acid catalysts produce high 2-aryl attachment when alkylating with alpha-olefins. See S. Sivasanker, A. Thangaraj, "Distribution of Isomers in the Alkylation of Benzene with Long-Chain Olefins over Solid Acid Catalysts," *Journal of Catalysis*, 138, 386–390 (1992).

Two general treatises on zeolite are; *Handbook of Molecular Sieves* by Rosemarie Szostak (Van Nostrand Reinhold, New York 1992) and *Molecular Sieves: Principles of Synthesis and Identification*, 2$^{nd}$ Edition, by Rosemarie Szostak (Chapman and Hall, London, UK 1999).

SUMMARY OF THE INVENTION

The present invention is directed to zeolite Y catalysts having a controlled macropore structure. The present invention is also directed to catalyst composites comprising zeolite Y catalyst and a process for preparing the catalyst composites. The catalysts and catalyst composites exhibit reduced deactivation rates during the alkylation process, thereby increasing the life of the catalysts and catalyst composites. The present invention is also directed to processes for preparation of carbonated, overbased alkylated aromatic sulfonates, which processes comprise the alkylation in the presence of the catalysts and catalyst composites of this invention, and further sulfonation and carbonation, overbasing of alkylated aromatic hydrocarbons.

In particular, the present invention is directed to a catalyst having a macropore structure comprising zeolite Y wherein the peak macropore diameter of the catalyst, measured by ASTM Test No. D 4284-03, is less than or equal to about 2000 angstroms, and the cumulative pore volume at pore diameters less than or equal to about 500 angstroms, measured by ASTM Test No. D 4284-03, is less than or equal to about 0.30 milliliters per gram, preferably less than about 0.30 milliliters per gram at pore diameters less than or equal to about 400 angstroms, and more preferably in the range of about 0.05 milliliters per gram to about 0.18 milliliters per gram at pore diameters less than or equal to about 400 angstroms.

The cumulative pore volume of the zeolite Y catalyst at pore diameters less than or equal to about 300 angstroms is preferably less than about 0.25 milliliters per gram, more preferably at pore diameters less than or equal to about 300 angstroms is less than about 0.20 milliliters per gram, and most preferably at pore diameters less than or equal to about 300 angstroms is in the range of about 0.08 milliliters per gram to about 0.16 milliliters per gram.

Preferably the peak macropore diameter of the zeolite Y catalyst is in the range of about 700 angstroms to about 1800 angstroms, and more preferably the peak macropore diameter is in the range of about 750 angstroms to about 1600 angstroms, and most preferably the peak macropore diameter is in the range of about 800 angstroms to about 1400 angstroms.

The zeolite Y catalyst of the present invention may have silica to alumina ratio of about 5:1 to about 100:1, preferably the silica to alumina ratio is from about 30:1 to about 80:1, and most preferably the silica to alumina ratio is from about 50:1 to about 70:1.

In an embodiment of the zeolite Y catalyst of the present invention, the catalyst is in the form of a tablet. The tablet may or may not include a binder. Preferably the peak macropore diameter of the zeolite Y catalyst tablet is in the range of about 500 angstroms to about 1500 angstroms, and the cumulative pore volume at pore diameters less than or equal to about 500 angstroms is in the range of about 0.05 milliliters per gram to about 0.15 milliliters per gram.

An embodiment of the present invention is directed to a catalyst composite comprising:
(a) the zeolite Y catalyst of the above invention; and
(b) a binder.

The binder in (b) above is a suitable inorganic material, preferably the binder is alumina.

The zeolite Y in the catalyst composite of the above embodiment is in the range of about 40 weight percent to about 99 weight percent based on the total dry weight of the catalyst composite. Preferably, zeolite Y in the catalyst composite is in the range of about 50 weight percent to about 85 weight percent based on the total dry weight of the catalyst composite.

A further embodiment of the present invention is directed to the process for preparing a catalyst composite comprising the steps of:
(a) contacting a zeolite Y powder with a binder in the presence of volatiles to form a mixture wherein the weight ratio of the zeolite Y is in the range of about 40 to about 99 based on the total dry weight of the resulting catalyst composite, and wherein the volatiles in the mixture are in the range of about 30 weight percent to about 70 weight percent;
(b) shaping the mixture to form a composite;
(c) drying the composite; and
(d) calcining the composite in a substantially dry environment.

The shaping in step (b) in the above process preferably comprises extruding.

The above process further comprises addition of a shaping aid in step (a). Preferably, the shaping aid is a polysaccharide.

The binder in step (a) above is a suitable inorganic material, preferably the binder is alumina.

The volatiles in step (a) in the process for making the zeolite Y composite comprise water and an acid, and preferably the acid is nitric acid.

The volatiles in step (a) in the above process for making the zeolite Y composite further comprise a polysaccharide.

The volatiles in the mixture in step (a) in the process for making the zeolite Y composite are in the range of about 40 weight percent to about 60 weight percent of the mixture.

In step (a) of the above process, the weight percent of the zeolite Y is in the range of about 50 to about 85.

A further embodiment of the present invention is directed to a catalyst composite made by the above process.

Another embodiment of the present invention is directed to a process for making an alkylated aromatic composition comprising contacting at least one aromatic hydrocarbon with at least one olefin under alkylation conditions in the presence of a catalyst having a macropore structure comprising zeolite Y wherein the peak macropore diameter of the catalyst, measured by ASTM Test No. D 4284-03, is less than or equal to about 2000 angstroms and cumulative pore volume of the catalyst at pore diameters less than or equal to about 500 angstroms, measured by ASTM Test No. D 4284-03, is equal to or less than about 0.30 milliliters per gram.

The above alkylation process is conducted without the addition of water and using dried aromatic hydrocarbon and olefin feed. It is believed that the presence of water during the alkylation increases the deactivation rate of the catalysts of this invention.

The above alkylation process further comprises sulfonating the alkylated aromatic composition to form an alkylated aromatic sulfonic acid.

The above process further comprises reacting the alkylated aromatic sulfonic acid an alkaline earth metal and carbon dioxide to produce a carbonated, overbased alkylated aromatic sulfonate.

Yet a further embodiment of the present invention is directed to a process for making an alkylated aromatic composition comprising contacting at least one aromatic hydrocarbon with at least one olefin under alkylation conditions in the presence of a catalyst composite comprising zeolite Y, and wherein the catalyst composite is prepared by the above process.

The aromatic hydrocarbon of the above process is benzene, toluene, xylene, cumene, or mixtures thereof. Preferably, the aromatic is benzene or toluene.

The olefin in the above process may be an alpha olefin, an isomerized olefin, a branched-chain olefin, or mixtures thereof. The olefin may have from about 4 carbon atoms to about 80 carbon atoms. The alpha olefin or the isomerized olefin may have from about 6 carbon atoms to about 40 carbon atoms, preferably from about 20 carbon atoms to about 40 carbon atoms. The branched-chain olefin may have from about 6 carbon atoms to about 70 carbon atoms, preferably from about 8 carbon atoms to about 50 carbon atoms, and more preferably from about 12 carbon atoms to about 18 carbon atoms.

The olefin in the above process may be a partially-branched-chain olefin containing from about 6 carbon atoms to about 40 carbon atoms, preferably from about 20 carbon atoms to about 40 carbon atoms.

The above alkylation process further comprises sulfonating the alkylated aromatic composition to form an alkylated aromatic sulfonic acid.

The above process further comprises reacting the alkylated aromatic sulfonic acid an alkaline earth metal and carbon dioxide to produce a carbonated, overbased alkylated aromatic sulfonate.

Yet a further embodiment of the present invention is directed to a process for making an alkylated aromatic composition comprising contacting at least one aromatic hydrocarbon with at least one olefin under alkylation conditions in the presence of a catalyst composite comprising zeolite Y, and wherein the catalyst composite is prepared by the above process.

The aromatic hydrocarbon of the above process is benzene, toluene, xylene, cumene, or mixtures thereof. Preferably, the aromatic is benzene or toluene.

The olefin in the above process may be an alpha olefin, an isomerized olefin, a branched-chain olefin, or mixtures thereof. The olefin may have from about 4 carbon atoms to about 80 carbon atoms. The alpha olefin or the isomerized olefin may have from about 6 carbon atoms to about 40 carbon atoms, preferably from about 20 carbon atoms to about 40 carbon atoms. The branched-chain olefin may have from about 6 carbon atoms to about 70 carbon atoms, preferably from about 8 carbon atoms to about 50 carbon atoms, and more preferably from about 12 carbon atoms to about 18 carbon atoms.

The olefin in the above process may be a partially-branched-chain olefin containing from about 6 carbon atoms to about 40 carbon atoms, preferably from about 20 carbon atoms to about 40 carbon atoms.

The above alkylation process is conducted without the addition of water and preferably using dried aromatic hydrocarbon and olefin feed. It is believed that the presence of water during the alkylation increases the deactivation rate of the catalysts of this invention.

The above alkylation process further comprises sulfonating the alkylated aromatic composition to form an alkylated aromatic sulfonic acid.

The above process further comprises reacting the alkylated aromatic sulfonic acid an alkaline earth metal and carbon dioxide to produce a carbonated, overbased alkylated aromatic sulfonate.

The process of the above embodiment of the present invention for making an alkylated aromatic composition further comprises the step of isomerizing normal alpha olefin with an isomerizing acidic catalyst before contacting the aromatic with the olefin to prepare an alkyl aromatic product where less than 40 weight percent of the alkylated aromatic hydrocarbon is 2-aryl, and at least 20 weight percent, preferably at least 75 weight percent of the alkylated aromatic hydrocarbon is a mono-alkylate.

Preferably, the acidic catalyst in the isomerization step is a solid catalyst having at least one metal oxide, which has an average pore size of less than 5.5 angstroms. More preferably, that acidic catalyst is a molecular sieve with a one-dimensional pore system.

DETAILED DESCRIPTION OF THE INVENTION

Definitions

The term "alkylate" means an alkylated aromatic hydrocarbon.

The term "2-aryl content" is defined as the percentage of total alkylate (the alkylate species in which the alkyl chain attached to the aromatic ring is derived from the olefin employed in the present alkylation process) that is comprised of those chemical species in which the attachment of the alkyl chain to the aromatic ring is at the 2-position along the alkyl chain.

The term "binder" means any suitable inorganic material which can serve as matrix or porous matrix to bind the zeolite particles into a more useful shape.

The term "branched-chain olefins" means olefins derived from the polymerization of olefin monomers higher than ethylene and containing a substantial number of branches wherein the branches are alkyl groups having from about one carbon atom to about 30 carbon atoms. Mixtures of ethylene and higher olefins are also contemplated.

The term "calcining" as used herein means heating the catalyst to about 400° C. to about 1,000° C. in a substantially dry environment.

The term "carbonated, overbased" is used to describe those alkaline earth metal alkyl aromatic sulfonates in which the ratio of the number of equivalents of the alkaline earth metal moiety to the number of equivalents of the aromatic sulfonic acid moiety is greater than one, and is usually greater than 10 and may be as high as 20 or greater.

The term "centrate" refers to a mixture of sludge fractions that were collected from prior carbonation, overbasing of alkylbenzene sulfonic acids similar to the sulfonic acids of the present invention. Centrate was produced during the purification of high TBN carbonated, overbased synthetic sulfonates by centrifugation and decantation at the end of the carbonation, overbasing reaction. Centrate was added to the carbonation, overbasing of alkylbenzene sulfonic acid reaction mixture in Example 11 in this patent application for recycling the contents of the centrate. Prior to its addition to the reaction mixture in Example 11, the centrate was characterized by determination of its TBN, the amount of xylene solvent, active calcium sulfonate, calcium hydroxide, calcium carbonate, carbon dioxide and 100 Neutral diluent oil.

The term "cumulative pore volume" obtained by Mercury Intrusion Porosimetry as used herein refers to that part of the total volume in milliliters per gram derived from the graphical, cumulative pore volume distribution, measured by Section 14.1.6 of ASTM D 4284-03, or the corresponding tabular presentation of the same data between defined upper and lower pore diameters. When no lower diameter limit is defined, the lower limit is the lowest detection limit or lowest radius measured by Section 14.1.6 of ASTM D 4284-03.

The terms "dry basis", "anhydrous basis", and "volatiles-free basis" shall refer to the dry weight of catalyst composite or raw materials expressed on a metal oxides basis such as $Na_2O \cdot Al_2O_3 \cdot xSiO_2$.

The term "loss-on-ignition (LOI)" as used herein means the percent weight loss of the zeolite composite or raw material samples when they are heated to 538° C. for 1 hour. When the temperature is greater than or equal to about 538° C., the "loss-on-ignition" approximates the percent volatiles.

The terms "macropore", "mesopore", and "micropore" as used herein follow the definitions set forth by the International Union of Pure and Applied Chemistry (IUPAC), Division of Physical Chemistry, in Manual of Symbols and Terminology for Physicochemical Quantities and Units, Appendix II Definitions, Terminology and Symbols in Colloid and Surface Chemistry Part I, Adopted by the IUPAC Council at Washington, D.C., U.S.A., on 23 July, 1971. Pores with widths or diameters exceeding ~50 nanometers (500 angstroms) are called "macropores". Pores with widths or diameters not exceeding ~2.0 nanometers (20 angstroms)

are called "micropores". Pores of intermediate size (2.0 nanometers<width or diameter≦50 nanometers) are called "mesopores".

The term "Mercury Intrusion Porosimetry" refers to the ASTM Test No. D 4284-03 used to determine pore volume distribution of catalysts by Mercury Intrusion Porosimetry. Mercury pore distribution was measured using a Quantachrome Scanning Mercury Porosimeter Model SP-100. The software version used by the instrument is V2.11 (dated Oct. 27, 1993). Surface tension used in the calculation is 473 dynes per centimeter and the contact angle is 140 degrees.

The terms "normal alpha olefin" and "linear alpha olefin" mean those straight-chain olefins without a significant degree of alkyl branching in which the carbon to carbon double bond resides primarily at the end or "alpha" position of the carbon chain, i.e., between $C_1$ and $C_2$. Normal alpha olefins are derived from polymerization of ethylene.

The term "normal alpha olefin isomerization" means the conversion of normal alpha olefins into isomerized olefins having a lower alpha olefin content (the double bond is between $C_1$ and $C_2$), higher internal olefin content (the double bond is in positions other than between $C_1$ and $C_2$), and optionally a higher degree of branching.

The term "partially-branched chain olefin" is defined as the olefin product of isomerization of normal alpha olefins wherein the degree of branching is higher than in the starting normal alpha olefins.

The term "peak macropore diameter" as used herein means the peak diameter (i.e., the diameter within the macropore region at which the differential plot of pore size distribution, as defined by Section 14.2, reaches a maximum) in the macropore range determined by ASTM Test No. D 4284-03 for the macropore peak in the catalysts of the present invention.

The term "peptizing" means the dispersion of large aggregates of binder particles, including hydrated aluminas, into much smaller primary particles by the addition of acid.

The term "percent volatiles" as used herein means the difference between the actual weight of the catalyst composite or the raw materials and the weight of the material on a dry, anhydrous, or volatiles-free basis, expressed as a percentage of the actual sample weight.

The terms "SAR" or "silica to alumina ratio" refer to the molar ratio of silicon oxide to aluminum oxide; mol $SiO_2$: mol $AlO_3$.

The term "sufficient water to shape the catalyst material" means quantity of water required to make an acid peptized mixture of zeolite and alumina powders into an extrudable mass.

The term "tabletting" as used herein refers to the process of forming a catalyst aggregate from zeolite powder or a mixture of zeolite and binder powders by compressing the powder in a die.

The term "total base number or TBN" refers to the amount of base equivalent to milligrams of KOH in one gram of sample. Thus, higher TBN numbers reflect more alkaline products, and therefore a greater alkalinity reserve. The TBN of a sample can be determined by ASTM Test No. D 2896 or any other similar procedure.

The term "total pore volume" obtained by Mercury Intrusion Porosimetry as used herein refers to the total pore volume in milliliters per gram derived from the graphical, cumulative pore volume distribution (Section 14.1.6 of ASTM D 4284-03) or the corresponding tabular presentation of the same data.

As used herein, all percentages are weight percent, unless otherwise specified.

As noted above, the present invention is directed to catalyst having a controlled macropore structure comprising zeolite Y. The catalysts of the present invention were characterized by pore volume distribution obtained by Mercury Intrusion Porosimetry, ASTM Test No. D 4284-03. Mercury Intrusion Porosimetry provides a graph of cumulative pore volume (pv) versus pore diameter (pd). Mercury Intrusion Porosimetry also is used to determine the macropore peak diameter from the derivative, delta pv ($\Delta$pv) divided by delta pd ($\Delta$pd). The graphs are used to characterize the catalysts of the present invention.

Zeolite Y catalysts and catalyst composites of the present invention when used in alkylation of aromatic hydrocarbons with olefins exhibited a substantial reduction in deactivation rates compared to zeolitic catalysts known in the prior art. This result was unexpected, since it had previously been believed that increasing the surface area of the catalyst would increase its activity, but was likely to also increase deactivation rates. Relative deactivation rates were determined for the catalysts of the present invention under standard alkylation reactions conditions. Results of the deactivation experiments are given in Table II. Reduction in deactivation rates of up to 75 percent and above were observed during alkylation reactions using these zeolitic Y catalysts and zeolite Y catalyst composites.

The zeolite Y catalysts and catalyst composites can be prepared using zeolite Y CBV 760® or CBV 600® available from Zeolyst International. Samples of these zeolite Y materials from which catalysts and catalyst composites of the present invention were prepared had a nominal silica to alumina ratio of ~60:1 and ~6.7:1, respectively. However, zeolite Y having a silica to alumina ratio between 5:1 and 120:1 may be used for the preparation of the zeolite Y catalysts and catalyst composites of the present invention.

The zeolite Y catalysts of the present invention may be shaped or formed into tablets, extrudates or any other shape using procedures well known in the prior art. The preparation of extrudates requires the presence of a binder, such as alumina. The tabletted catalysts do not require the presence of a binder, but a binder may be present in a tabletted zeolite catalyst. The crystalline zeolite powder may be compressed to form a tablet. The tabletted catalysts of the present invention provide exceptionally low deactivation rates in alkylation reactions.

The alkylation reaction may be carried out by any conventionally known process without the addition of water and using a dried aromatic hydrocarbon and olefin feed. It is believed that the presence of water during the alkylation increases the deactivation rate of the catalysts of this invention. The aromatic hydrocarbon is reacted with one or more olefins in the presence of a catalyst of the present invention under alkylation reaction conditions. The aromatic hydrocarbon may be single-ring or double-ring, preferably the aromatic hydrocarbon is a single-ring aromatic hydrocarbon. The aromatic hydrocarbon may be an alkylated aromatic hydrocarbon, such as a mono-alkylated aromatic hydrocarbon, wherein the alkyl group has from about 4 carbon atoms to about 80 carbon atoms. When the aromatic hydrocarbon used is a mono-alkylated aromatic, the product of the alkylation reaction is a di-alkylated aromatic.

The olefins useful for alkylation of the aromatic hydrocarbons may be linear-chain olefins or branched-chain olefins having from about 4 carbon atoms to about 80 carbon atoms. In addition, normal alpha olefins may be isomerized to obtain partially-branched-chain olefins for use in alkylation reaction of the present invention. These resulting partially-branched-chain olefins may be alpha-olefins, beta-olefins, internal-olefins, tri-substituted olefins, and vinylidene olefins.

Alkylated aromatic hydrocarbon sulfonic acids of the alkylated aromatic hydrocarbons of the present invention may be prepared by any known sulfonation reaction. The alkylated aromatic sulfonic acids may be further reacted with an alkaline earth metal and carbon dioxide to obtain carbonated, overbased alkylated aromatic sulfonates useful as detergents in lubricating oils. Carbonation may be carried out by any conventionally known process. The degree of overbasing may be controlled by changing the reaction conditions and the amount of the alkaline earth metal and carbon dioxide used in the carbonation process.

Procedure for Isomerization of Normal Alpha Olefins

The isomerization process may be carried out in batch or continuous mode. The process temperatures can range from 50° C. to 250° C. In the batch mode, a typical method is to use a stirred autoclave or glass flask, which may be heated to the desired reaction temperature. A continuous process is most efficiently carried out in a fixed bed process. Space rates in a fixed bed process can range from 0.1 to 10 or more weight hourly space velocity.

In a fixed bed process, the isomerization catalyst is charged to the reactor and activated or dried at a temperature of at least 150° C. under vacuum or flowing inert, dry gas. After activation, the temperature of the isomerization catalyst is adjusted to the desired reaction temperature and a flow of the olefin is introduced into the reactor. The reactor effluent containing the partially-branched, isomerized olefins is collected. The resulting partially-branched, isomerized olefins contain a different olefin distribution (alpha olefin, beta olefin; internal olefin, tri-substituted olefin, and vinylidene olefin) and branching content than the unisomerized olefin.

Procedure for Alkylation of Aromatic Hydrocarbons

Alkylation of aromatic hydrocarbons with normal alpha olefins, partially-branched-chain isomerized olefins, and branched-chain olefins may be carried out by any method known by a person skilled in the art.

The alkylation reaction is typically carried out with an aromatic hydrocarbon and an olefin in molar ratios from 1:15 to 25:1. Process temperatures can range from about 100° C. to about 250° C. The process is carried out without the addition of water. As the olefins have a high boiling point, the process is preferably carried out in the liquid phase. The alkylation process may be carried out in batch or continuous mode. In the batch mode, a typical method is to use a stirred autoclave or glass flask, which may be heated to the desired reaction temperature. A continuous process is most efficiently carried out in a fixed bed process. Space rates in a fixed bed process can range from 0.01 to 10 or more weight hourly space velocity.

In a fixed bed process, the alkylation catalyst is charged to the reactor and activated or dried at a temperature of at least 150° C. under vacuum or flowing inert, dry gas. After activation, the alkylation catalyst is cooled to ambient temperature and a flow of the aromatic hydrocarbon compound is introduced, optionally toluene. Pressure is increased by means of a back pressure valve so that the pressure is above the bubble point pressure of the aromatic hydrocarbon feed composition at the desired reaction temperature. After pressurizing the system to the desired pressure, the temperature is increased to the desired reaction temperature. A flow of the olefin is then mixed with the aromatic hydrocarbon and allowed to flow over the catalyst. The reactor effluent comprising alkylated aromatic hydrocarbon, unreacted olefin and excess aromatic hydrocarbon compound are collected. The excess aromatic hydrocarbon compound is then removed by distillation, stripping, evaporation under vacuum, or any other means known to those skilled in the art.

Procedure for Sulfonation of Alkylated Aromatic Hydrocarbons

Sulfonation of alkylated hydrocarbons may be carried out by any method known by a person skilled in the art.

The sulfonation reaction is typically carried out in a falling film tubular reactor maintained at about 65° C. The alkylated aromatic hydrocarbon is placed in the tube and sulfur trioxide diluted with nitrogen is added to the alkylated aromatic hydrocarbon. The molar ratio of alkylated aromatic hydrocarbon to sulfur trioxide is maintained at about 1.05:1. The resulting alkylated aromatic sulfonic acid may be diluted with about 10% 100 Neutral oil followed by thermal treatment with nitrogen bubbling at a rate of about 10 liters per kilogram of product and stirring while maintaining the temperature at about 85° C. until the desired residual sulfuric acid content is obtained (maximum of about 0.5%).

Procedure for Carbonation, Overbasing of Alkylated Aromatic Sulfonic Acids

Carbonation, overbasing of alkylaromatic sulfonic acids may be carried out by any method known by a person skilled in the art to produce alkylaromatic sulfonates.

Generally, the carbonation, overbasing reaction is carried out in a reactor in the presence of the alkylated aromatic sulfonic acid, diluent oil, an aromatic solvent, and an alcohol. The reaction mixture is agitated and alkaline earth metal and carbon dioxide are added to the reaction while maintaining the temperature between about 20° C. and 80° C.

The degree of carbonation, overbasing may be controlled by the quantity of the alkaline earth metal and carbon dioxide added to the reaction mixture, the reactants and the reaction conditions used during the carbonation process.

EXAMPLES

Preparation of Zeolite Y Alkylation Catalyst Composite

Example 1

Preparation of Catalyst Composite 1

Zeolite Y alkylation catalyst composites were prepared by the following method:

Loss-on-ignition (LOI) was determined for a sample of a commercially available zeolite Y CBV 760® available from Zeolyst International by heating the sample to 538° C. for 1 hour. The LOI obtained was 14.65 weight % and provided the percent volatiles in the zeolite Y batch being used. The LOI of a commercial sample of Versal® hydrated aluminum oxide available from Kaiser LaRoche Hydrate Partners was determined by heating the sample to 538° C. for 1 hour and was 24.87 weight %. Next, based on the results obtained from the LOI, 1875 grams of zeolite Y powder and 532 grams of alumina powder were weighed out to give a total of 1600 grams of zeolite powder and 400 grams of alumina powder on a volatile-free basis. Extrusion aid, Methocell®, 60 grams, available from Dow Corning, was added to the mixture of the two powders.

The two dry powders were added to a Baker Perkins mixer and dry mixed for 4 minutes. The amount of concentrated (70.7%) nitric acid to give 0.7 weight % (based on 100% nitric acid) of the dry weight of the zeolite and the alumina powders was calculated to be 19.8 grams. This amount of 70.7% nitric acid was weighed out and dissolved in 200 grams of deionized water.

The total amount of water and 70.7% nitric acid needed to obtain a final concentration of approximately 50% total volatiles was calculated as follows. Volatiles in the Y zeolite powder are 274.67 grams (1874.67 gram total weight−1600 grams dry weight). Volatiles in the alumina powder are 232.40 grams (532.4 grams total weight−400 grams dry weight). Nitric acid solution and Methocell® extrusion aid are considered to be 100% volatiles. Thus, if all the above raw materials were combined, the volatiles would be 786.87 grams. To give a mixture of 2000 grams (1600 grams zeolite and 400 grams alumina) dry powder with 50% volatiles, the total weight of the mixture must be 4000 grams. Thus, an additional 1213.13 grams of deionized water must be added.

To the powders in the mixer, 1250 grams of deionized water were added over a period of 5 minutes using a peristaltic pump. The mixer was then stopped so that the walls of the mixer could be scraped down. Mixing was then resumed and the solution of nitric acid in water was added over 5 minutes using the peristaltic pump. At the end of acid addition, mixing was continued for a total time of 40 minutes, with occasional holds to allow for scraping the sides of the mixer. At the end of the mixing period, the mixture was still powdery and the volatiles were measured as 48.83 weight %. Additional amounts of deionized water 10 grams at a time were added with 5 minutes mixing for each addition until the mixture appeared extrudable. A total of 85 grams of additional water was added over 1 hour and 45 minutes. At this point, the volatiles were 48.36 weight %.

The wet mixture was extruded through 1.27 millimeters, asymmetric quadrilobe die inserts, in a Bonnot extruder. The wet long cylindrical strands were dried at 121° C. for 8 hours. The long cylindrical strands were then broken to give extrudates with length to diameter ratio of 2:6. The extrudates were sieved and the portion larger than 1 millimeter was retained.

The extrudates were then calcined in a substantially dry environment in a muffle furnace using the following temperature program:

The extrudates were heated to 593° C. over two hours, then held at 593° C. for ½ hour and next cooled to 204° C. A total of 1681 grams of extrudates were obtained.

Mercury Intrusion Porosimetry showed the extrudates to have a peak macropore diameter of 1167 angstroms and a cumulative pore volume at diameters less than 300 angstroms of 0.1400 ml/gram.

Example 2

Preparation of Catalyst Composite 2

Zeolite Y catalyst was prepared following the procedure used in Example 1 above, with the following exceptions:

Catapal B® alumina available from Vista Chemical Company was used instead of Versal® alumina. The total amount zeolite Y and alumina powders were scaled to 1300 grams dry weight. Methocell® extrusion aid was not added. Volatiles of the zeolite powder and alumina powder were 9.72 weight % and 24.82 weight %, respectively. Concentrated nitric acid, 12.9 grams, was dissolved in 300 grams deionized water. In the Baker Perkins mixer, 671.7 grams of deionized water were added in 10 minutes, followed by the acid solution in 10 minutes. After mixing for 40 minutes, volatiles were 47.18 weight %, but the mixture was too thick to extrude. With an additional 3 hours of mixing, the mixture was still not extrudable. Over the next 30 minutes, an additional 10 grams of deionized water was added. The mixture was then extruded, dried, and calcined in a substantially dry environment.

Mercury Intrusion Porosimetry showed the peak macropore diameter to be 878 angstroms and the cumulative pore volume at diameters less than 300 angstroms to be 0.1424 ml/gram.

Example 3

Preparation of Catalyst Composite 3

This catalyst was made by the procedure described in Example 2 above with the following exceptions:

Volatiles of the zeolite Y powder and alumina powder were 12.24 weight % and 23.89 weight %, respectively. Corresponding amounts of zeolite and alumina powders were 1185 grams and 342 grams, respectively. Added deionized water was 580 grams. After 50 minutes of mixing, the mixture was still granular. A good paste was obtained after mixing for 1 hour 30 minutes. Volatiles were 46.8 weight % at extrusion time. After extruding, drying, sizing, and calcining in a substantially dry environment, Mercury Intrusion Porosimetry showed the peak macropore diameter to be 1006 angstroms and the cumulative pore volume at diameters less than 300 angstroms to be 0.1400 ml/gram.

Example 4

Preparation of Catalyst Composite 4

This catalyst was made by the procedure described in Example 2 with the following exceptions:

Volatiles of the zeolite Y powder and alumina powder were 14.36 weight % and 27.54 weight %, respectively. Corresponding amounts of zeolite and alumina powders were 747.4 grams and 220.8 grams, respectively. The final weight % of the nitric acid of the dry weight of the zeolite and the alumina in this preparation was 0.75%. The acid was dissolved in 655.8 grams of deionized water. The powders were mixed in a plastic bag for 3 minutes and then mixed in the Baker Perkins mixer for 3 minutes. The acid solution was pumped in over 8 minutes while continued mixing. At 10 minutes after completion of acid addition, the mixture became pasty. Mixing was continued for an additional 30 minutes. Volatiles were 49.0 weight %. The wet mix was extruded, dried, and sized.

The extrudates were calcined in a substantially dry environment in a muffle furnace according to the following temperature program:

The extrudates were heated at full power to 593° C. Temperature overshoot was avoided. Next, the extrudates were held at 593° C. for one hour and cooled to 149° C. Mercury Intrusion Porosimetry showed the peak macropore diameter to be 1486 angstroms and the cumulative pore volume at diameters less than 300 angstroms to be 0.1494 ml/gram.

Example 5

Preparation of Catalyst 5

Tabletted zeolite Y catalyst was prepared by a custom catalyst manufacturer using a sample of the zeolite Y CBV 760® available from Zeolyst International. The tablets were cylinders, ⅛ inch in diameter and approximately ⅛ inch in length. Mercury Intrusion Porosimetry showed the peak macropore diameter to be 815 angstroms and the cumulative pore volume at diameters less than 300 angstroms to be 0.0844 ml/gram.

Example 6

Preparation of Catalyst 10

This catalyst was made by the procedure described in Example 2 with the following exceptions:

Volatiles of the zeolite Y powder and alumina powder were 18.7 weight % and 26.5 weight %, respectively. Corresponding amounts of zeolite and alumina powders were 639.6 grams and 276.9 grams, respectively. The final weight % of the nitric acid of the dry weight of the zeolite and the alumina in this preparation was 0.75% and 6.44 grams of nitric acid was dissolved in 150 grams of deionized water. The powders were mixed in a plastic bag for 15 minutes and then mixed in the Baker Perkins mixer for 10 minutes. An additional 276.9 grams of deionized water was pumped into the mixture over 20 minutes while mixing. The acid solution was pumped in over 8 minutes with continued mixing. Mixing was continued for an additional 30 minutes. Volatiles were 46.40 weight %. The wet mix was extruded, dried, and sized.

The extrudates were calcined in a substantially dry environment in a muffle furnace according to the following temperature program:

The extrudates were heated at full power to 593° C. Temperature overshoot was avoided. Next, the extrudates were held at 593° C. for one hour and cooled to 149° C. Mercury Intrusion Porosimetry showed the peak macropore diameter to be 941 angstroms and the cumulative pore volume at diameters less than 300 angstroms to be 0.155 ml/gram.

Example 7

Preparation of Catalyst 12

This catalyst was made by the procedure described in Example 2 with the following exceptions:

Volatiles of the zeolite powder and alumina powder were 12.24 weight % and 23.89 weight %, respectively. Corresponding amounts of zeolite and alumina powders were 1185.1 grams and 341.6 grams, respectively. The final weight % of the nitric acid of the dry weight of the zeolite and the alumina in this preparation was 0.75% and 12.9 grams of nitric acid was dissolved in 300 grams of deionized water. The powders were mixed in a plastic bag for 5 minutes and then mixed in the Baker Perkins mixer for 5 minutes. Additional deionized water, 619.7 grams, was added to the mixture over 20 minutes. The acid solution was pumped in over 8 minutes with continued mixing. Mixing was continued for an additional 40 minutes. At this time, the mixture was still a powder. After 3 hours of mixing, an additional 50 grams of deionized water was added to the mixture. After 3½ hours of *mixing*, an additional 25 grams of deionized water was added to the mixture and another 15 grams of deionized water was added to the mixture after 4 hours and 4¼ hours of *mixing*. After 4 hours and 55 minutes of mixing, the volatiles were 45.2 weight %. The wet mix was extruded, dried, and sized.

The extrudates were calcined in a substantially dry environment in a muffle furnace according to the following temperature program:

The extrudates were heated at full power to 593° C. Temperature overshoot was avoided. Next, the extrudates were held at 593° C. for one hour and cooled to 149° C. Mercury Intrusion Porosimetry showed the peak macropore diameter to be 900 angstroms and the cumulative pore volume at diameters less than 300 angstroms to be 0.144 ml/gram.

The Mercury Intrusion Porosimetry results for the zeolite Y catalysts of Examples 1–7 (Catalyst Composites 1–5, 10 and 12) are given below in Table I.

TABLE I

| | Mercury Intrusion Porosimetry Properties | | |
|---|---|---|---|
| Catalyst Composite | Total PV* (ml/gram) | PV < 300 angstroms** (ml/gram) | Macropore peak diameter (angstroms) |
| 1 | 0.4612 | 0.140 | 1167 |
| 2 | 0.4207 | 0.142 | 878 |
| 3 | 0.4208 | 0.140 | 1006 |
| 4 | 0.4492 | 0.149 | 1486 |
| 5*** | 0.3914 | 0.084 | 815 |
| 10 | 0.403 | 0.155 | 941 |
| 12 | 0.399 | 0.144 | 900 |

*Total pore volume.
**Total pore volume at diameters less than or equal to 300 angstroms.
***Catalyst 5 is not a composite. Catalyst 5 is a tabletted zeolite Y powder, prepared as described above in Example 5.

Example 8

Preparation of Isomerized Normal Alpha Olefins

Typically, isomerization of normal alpha olefins is carried out as described below:

$C_{20}$–$C_{24}$ normal alpha olefin with the following composition was used for this Example:

Alpha olefin 89.1%

Beta olefin 0.5%

Internal olefin 1.4%

Tri-substituted olefin 0.2%

Vinylidene olefin 9.5% (determined by carbon nuclear magnetic resonance spectroscopy)

Branched-chain olefin 11% (determined by infra red spectroscopy)

The normal alpha olefin was pumped up-flow through a fixed-bed reactor (570 millimeters high and with an inside diameter of 22.3 millimeters) containing 65 grams of solid olefin isomerization. The reactor was operated isothermally at 160° C. at a liquid to hourly space velocity of 0.5 per hour and at atmospheric pressure.

The reactor effluent containing the partially branched, isomerized olefin is collected. The resulting partially-branched, isomerized olefin contains a different olefin distribution (alpha-olefin, beta-olefin; internal-olefin, tri-substituted-olefin, and vinylidene-olefin) and branching content than the un-isomerized olefin.

Example 9

Preparation of Alkylbenzene Compositions

Typically, alkylation of aromatic hydrocarbons with normal alpha olefins, partially-branched-chain isomerized olefins and branched-chain olefins was carried out as described below:

A fixed bed reactor constructed from 15.54 millimeters internal diameter Schedule 160 stainless steel pipe was used for this alkylation test. Pressure in the reactor was maintained by an appropriate back pressure valve. The reactor and heaters were constructed so that adiabatic temperature control could be maintained during the course of alkylation runs. A 192 gram bed of 850 micrometer to 2 millimeters Alundum particles was packed in the bottom of the reactor to provide a pre-heat zone. Next, 100 grams of Catalyst Composite 12 was charged to the fixed bed reactor. The reactor was gently vibrated during loading to give a maximum packed bulk density of catalyst in the reactor. Finally, void spaces in the catalyst bed were filled with 351 grams 150 micrometers Alundum particles as interstitial packing.

The reactor was then closed, sealed, and pressure tested under nitrogen. Next the alkylation catalyst was dehydrated during 15 hours at 200° C. under a 20 liters per hour flow of nitrogen measured at ambient temperature and pressure and then cooled to 100° C. under nitrogen. Benzene was then introduced into the catalytic bed in an up-flow manner at a flow rate of 195 grams per hour. Temperature (under adiabatic temperature control) was increased to a start-of-run temperature of 182° C. (measured just before the catalyst bed) and the pressure was increased to 14.6 atmospheres.

When temperature and pressure had lined out at desired start-of-run conditions of 182° C. and 14.6 atmospheres, a feed mixture, consisting of benzene and $C_{20-24}$ NAO at a molar ratio of 10:1 and dried over activated alumina, was introduced in an up-flow manner. As the feed reached the catalyst in the reactor, reaction began to occur and internal catalyst bed temperatures increased above the inlet temperature. After about 8 hours on-stream, the reactor exotherm was 20° C. At 26 hours on-stream, the olefin conversion in the product was 99.1%. The run was stopped after 408 hours on-stream, although the run could have continued. At this time, the olefin conversion was 99.45%.

Alkylated aromatic hydrocarbon products containing excess benzene were collected during the course of the run. After distillation to remove excess aromatic hydrocarbon, analysis showed that greater than 99% conversion of olefin was achieved during the course of the run.

Example 10

Preparation of Alkylated Benzene Sulfonic Acids

The alkylbenzene alkylate produced as in Example 9 above was sulfonated by a concurrent stream of sulfur trioxide ($SO_3$) and air with in a tubular reactor (2 meters long and 1 centimeter inside diameter) in a down flow mode using the following conditions:

Reactor temperature was 60° C., $SO_3$ flow rate was 73 grams per hour, alkylate flow rate was 327 grams per hour at a $SO_3$ to alkylate molar ratio of 1.05. The $SO_3$ was generated by passing a mixture of oxygen and sulfur dioxide ($SO_2$) through a catalytic furnace containing vanadium oxide ($V_2O_5$).

The resulting crude alkylbenzene sulfonic acid had the following properties based on the total weight of the product: the weight % of $HSO_3$ was 16.1 and the weight % of $H_2SO_4$ was 1.35.

The crude alkylbenzene sulfonic acid was diluted with 10 weight % 100 Neutral diluent oil based on the total weight of the crude alkylbenzene sulfonic acid and placed in a four liter four-neck glass reactor fitted with a stainless steel mechanical agitator rotating at between 300 and 350 rpm, a condenser and a gas inlet tube (2 millimeters inside diameter) located just above the agitator blades for the introduction of nitrogen gas. The contents of the reactor was heated to 85° C. with stirring and nitrogen gas was bubbled through the mixture between 30–40 liters per hour for between about 4 to 6 hours until the weight % of $H_2SO_4$ is less than about 0.3 weight % based on the total weight of the product. This material is the final alkylbenzene sulfonic acid.

The final alkylbenzene sulfonic acid had the following properties based on the total weight of the product: weight % of $HSO_3$ was 15.76 and weight % of $H_2SO_4$ was 0.15.

Example 11

Preparation of Carbonated, Overbased Alkylated Benzene Sulfonates

To a 5 liter four-neck reactor equipped with heating and cooling capability and fitted with a stainless steel mechanical agitator rotating at between 300 and 350 rpm, a gas inlet tube (2 millimeters inside diameter) located just above the agitator blades for the addition of $CO_2$, a distillation column and condenser under nitrogen gas was charged 123.7 grams of centrate.

The centrate was a mixture of the sludge fractions previously produced during the purification of high TBN carbonated, overbased synthetic sulfonates by centrifugation and decantation and was added to the reaction mixture of this example for recycling the contents of the centrate. The centrate had a TBN of 206 and contained approximately 68 grams of xylene solvent, 11 grams active calcium sulfonate, 8 grams calcium hydroxide and calcium carbonate, 8 grams of carbon dioxide, and 22 grams of 100 Neutral diluent oil isolated.

Next, 40 grams of methanol, 207 grams of xylene solvent, 281 grams (0.59 mole) of the alkylbenzene sulfonic acid ($HSO_3$ was 15.8 weight % based on the total weight of the reaction mixture) from Example 10 above was charged to the reactor over 15 minutes at room temperature. A slurry of 160 grams (2.16 mole) of calcium hydroxide, 365 grams of xylene solvent, and 94.2 grams of methanol was added to the reactor and the reactor was cooled to 25° C. Next, 35 grams (0.79 mole) of $CO_2$ was added to the reaction mixture through the gas inlet tube over 39 minutes while the temperature of the reactor increased to about 32° C. A second slurry composed of 160 grams (2.16 mole) of calcium hydroxide, 384 grams xylene solvent, and 131 grams of methanol was then added to the reactor concurrently with 0.9 grams of $CO_2$ over about 1 minute. Next, 92 grams of $CO_2$ was added to the reactor over 64 minutes while the temperature of the reactor increased from about 30° C. to 41° C. A third slurry composed of 82 grams of calcium hydroxide and 298 grams of xylene solvent was then charged to the reactor concurrently with 1.4 grams of $CO_2$ over about 1 minute. Next, 55 grams (1.25 mole) of $CO_2$ was added to the reactor over approximately 60 minutes while keeping the reactor temperature at approximately 38° C.

The water and methanol were then distilled from the reactor by first heating the reactor to 65° C. over 40 minutes at atmospheric pressure, then to 93° C. over 60 minutes at atmospheric pressure, and then 130° C. over 30 minutes at atmospheric pressure. The temperature of the reactor was then decreased to 110° C. over 60 minutes at atmospheric pressure and next held at 110° C. for 30 minutes at atmospheric pressure. The contents of the reactor were then cooled to approximately 30° C. and 510 grams of 600 Neutral diluent oil was added to the reactor followed by 413 grams of xylene solvent. The sediment in the product was then removed by centrifugation. The xylene solvent in the product was distilled by heating the product to 204° C. over approximately 45 minutes at 30 millimeters Hg vacuum and holding the product at 204° C. and 30 millimeters Hg vacuum for 10 minutes. The vacuum was replaced with nitrogen gas and the contents were allowed to cool to room temperature to afford the carbonated, overbased sulfonate with the following properties based on the total weight of the product:

the catalyst bed. Using temperature profile data from a catalyst run, the position of the temperature exotherm in the bed was plotted as a function of time, in hours. The deactivation rate of the catalyst is the slope of this line in centimeters per hour. All catalysts were evaluated at standard conditions of temperature, pressure, and space velocity and the deactivation rates were measured.

Catalyst Composites 1, 2, 4, 5, 10 and 12 are the Catalyst Composites prepared in Examples 1–7 and shown in Table I above with the exception that Catalyst Composite 2 in Table II is a mixture of batches of Catalyst Composite 2 in Table I.

Test 1 was conducted during alkylation of toluene with an isomerized $C_{20}$ to $C_{24}$, low alpha content olefin at a temperature of 170° C. The molar ratio of toluene to olefin was 6.

Test 2 was conducted during alkylation of benzene with a $C_{20}$ to $C_{24}$ normal alpha olefin at a temperature of 180° C. The molar ratio of toluene to olefin was 10.

Deactivation rates are shown relative to the deactivation rate of Catalyst Composite 8 and Catalyst Composite 11 and are given in Table II below.

TABLE II

| Catalyst Composite | % zeolite in Catalyst | Nominal Zeolite SAR* | Mercury Intrusion Porosimetry Properties | | | Relative Deactivation Rate | |
|---|---|---|---|---|---|---|---|
| | | | Total PV* (ml/gram) | PV < 300 Å (ml/gram) | Macropore peak diameter, Å | Test 1 | Test 2 |
| 1 | 80 | 60 | 0.461 | 0.140 | 1167 | 86 | — |
| 2** | 80 | 60 | 0.436 | 0.156 | 931 | 61 | 46 |
| 4 | 80 | 60 | 0.449 | 0.149 | 1486 | — | 50 |
| 5 | 100 | 60 | 0.391 | 0.084 | 815 | — | 23 |
| 6 | 80 | 60 | 0.596 | 0.182 | 1664 | 67 | — |
| 7 | 65 | 6.7 | 0.488 | 0.270 | 1376 | 90 | — |
| 8 | 70 | 6.7 | 0.465 | 0.200 | 1591 | 100 | — |
| 9 | 80 | 60 | 0.575 | 0.174 | 1513 | 73 | — |
| 10 | 80 | 60 | 0.403 | 0.155 | 941 | 35 | — |
| 11 | 80 | 60 | 0.463 | 0.179 | 1110 | 43 | — |
| 12 | 80 | 60 | 0.399 | 0.144 | 900 | — | 35 |
| 13 | 80 | 60 | 0.449 | 0.163 | 1157 | — | 48 |
| 14 | 80 | 60 | 0.404 | 0.146 | 962 | — | 46 |
| 15 | 80 | 60 | 0.505 | 0.155 | 1738 | — | 100 |
| 16 | 80 | 60 | 0.444 | 0.162 | 1244 | — | 54 |
| 17 | 80 | 60 | 0.415 | 0.162 | 1031 | — | 46 |
| 18 | 80 | 60 | 0.421 | 0.136 | 1256 | — | 38 |

*Silica to alumina ratio in the crystalline zeolite powder.
**Catalyst Composite 2 in Table II was prepared as the Catalyst Composite 2 in Table I, except that Catalyst Composite 2 in Table II contained more than one batch of catalysts composites prepared in the manner of Catalyst Composite 2 of Table I.

Weight % calcium was 16.1, TBN was 424, weight % of sulfur was 1.81, weight % of calcium sulfonate was 0.87, and viscosity was 101 cSt at 100° C.

Example 12

Procedure for Measuring Deactivation Rates of the Catalysts in Alkylation Reactions Deactivation rates of the alkylation catalysts were measured during the alkylation reaction similar to the alkylation reaction in Example 9 above.

The alkylation reaction was carried out as described above under adiabatic temperature control. As the alkylation reaction was exothermic, a temperature exotherm was measured by means of appropriately located thermocouples in Effect of Silica to Alumina Ratio on Reduction in Deactivation Rate Without being bound by any theory, it is believed that the higher silica to alumina ratio and percent zeolite in the catalyst are important for obtaining greater degree of reduction in relative deactivation rates with the catalyst composites of this invention. In Table III, Catalysts 6 and 8 have similar macropore peak diameters and cumulative pore volumes, but very different silica to alumina ratios. By increasing the silica to alumina ratio from 6.7 to 60 and percent zeolite from 70 percent to 80 percent, the relative deactivation rate of 100 of Catalyst 8 is reduced to 67 of Catalyst 6.

TABLE III

| Catalyst Composite | % zeolite in Catalyst | Nominal Zeolite SAR* | Mercury Intrusion Porosimetry Properties | | | Relative Deactivation Rate Test 1 |
| --- | --- | --- | --- | --- | --- | --- |
| | | | Total PV* (ml/gram) | PV < 300 Å (ml/gram) | Macropore peak diameter, Å | |
| 6 | 80 | 60 | 0.596 | 0.182 | 1664 | 67 |
| 8 | 70 | 6.7 | 0.465 | 0.200 | 1591 | 100 |

Effect of Peak Macropore Diameter on Reduction in Deactivation Rate

Without being bound by any theory, it is believed that the peak macropore diameter has an effect on the deactivation rate of the catalyst composites of this invention. A higher peak macropore diameter results is a higher relative deactivation rate. In Table IV, Catalyst Composites 9 and 10 are compared because, although they both differ slightly in the cumulative pore volume, 174 versus 155, Catalyst Composite 9 has a much higher peak macropore diameter and a much higher relative deactivation rate, 1513 and 73, compared to Catalyst Composites 10, 941, and 35.

TABLE IV

| Catalyst Composite | % zeolite in Catalyst | Nominal Zeolite SAR* | Mercury Intrusion Porosimetry Properties | | | Relative Deactivation Rate Test 1 |
| --- | --- | --- | --- | --- | --- | --- |
| | | | Total PV* (ml/gram) | PV < 300 Å (ml/gram) | Macropore peak diameter, Å | |
| 9 | 80 | 60 | 0.575 | 0.174 | 1513 | 73 |
| 10 | 80 | 60 | 0.403 | 0.155 | 941 | 35 |

Effect of Cumulative Pore Volume on Deactivation Rate

Without being bound by any theory, it is believed that lowering the cumulative pore volume at pore diameters less than or equal to 300 angstroms results in lower deactivation rates. In Table V, Catalyst Composites 16 and 18 differ only by the cumulative pore volume, 162 and 136, respectively, and Catalyst Composite 16 has a higher relative deactivation rate, 54, compared to Catalyst Composites 18, 38.

TABLE V

| Catalyst Composite | % zeolite in Catalyst | Nominal Zeolite SAR* | Mercury Intrusion Porosimetry Properties | | | Relative Deactivation Rate Test 2 |
| --- | --- | --- | --- | --- | --- | --- |
| | | | Total PV* (ml/gram) | PV < 300 Å (ml/gram) | Macropore peak diameter, Å | |
| 16 | 80 | 60 | 0.444 | 0.162 | 1244 | 54 |
| 18 | 80 | 60 | 0.421 | 0.136 | 1256 | 38 |

What is claimed is:

1. A process for preparing an alkylated aromatic composition comprising:
   contacting at least one aromatic hydrocarbon with at least one olefin under alkylation conditions in the presence of a catalyst having a macropore structure comprising zeolite Y wherein the peak macropore diameter, measured by ASTM Test No. D 4284-03, is less than about 2000 angstroms and the cumulative pore volume of the catalyst at pore diameters less than or equal to about 500 angstroms, measured by ASTM Test No. D 4284-03, is less than or equal to about 0.30 milliliters per gram.

2. The process of claim 1 further comprising sulfonating the alkylated aromatic composition to form an alkylated aromatic sulfonic acid.

3. The process of claim 2 further comprising reacting the alkylated aromatic sulfonic acid with an alkaline earth metal and carbon dioxide to produce a carbonated, overbased alkylated aromatic sulfonate.

4. The process of claim 1, wherein the catalyst is a composite produced by
   (a) contacting a zeolite Y with a binder in the presence of volatiles to form a mixture wherein the weight percent of zeolite Y is in the range of about 40 to about 99 percent based on the total dry weight of the resulting catalyst composite, and wherein the volatiles in the mixture are in the range of about 30 weight percent to about 70 weight percent of the mixture;
   (b) shaping the mixture to form a composite;
   (c) drying the composite; and
   (d) calcining the composite in a substantially dry environment.

5. The process of claim 4 wherein the aromatic hydrocarbon is benzene or toluene.

6. The process of claim 4 wherein the olefin is an alpha olefin, an isomerized olefin, a branched-chain olefin or mixtures thereof.

7. The process of claim 6 wherein the olefin has from about 4 carbon atoms to about 80 carbon atoms.

8. The process of claim 6 wherein the alpha olefin or the isomerized olefin have from about 6 carbon atoms to about 40 carbon atoms.

9. The process of claim 8 wherein alpha olefin or the isomerized olefin have from about 20 carbon atoms to about 40 carbon atoms.

10. The process of claim 6 wherein the branched-chain olefin has from about 6 carbon atoms to about 70 carbon atoms.

11. The process of claim 10 wherein the branched-chain olefin has from about 8 carbon atoms to about 50 carbon atoms.

12. The process of claim 11 wherein the branched-chain olefin has from about 12 carbon atoms to about 18 carbon atoms.

13. The process of claim 6 wherein the olefin is a partially-branched-chain isomerized olefin wherein the olefin has from about 6 carbon atoms to about 40 carbon atoms.

14. The process of claim 13 wherein the partially-branched-chain isomerized olefin has from about 20 carbon atoms to about 40 carbon atoms.

15. The process of claim 4 further comprising sulfonating the alkylated aromatic composition to form an alkylated aromatic sulfonic acid.

16. The process of claim 15 further comprising reacting the alkylated aromatic sulfonic acid with an alkaline earth metal and carbon dioxide to produce a carbonated, overbased alkylated aromatic sulfonate.

* * * * *